United States Patent
Kubota et al.

(10) Patent No.: US 8,681,152 B2
(45) Date of Patent: Mar. 25, 2014

(54) METHOD FOR GENERATING MODEL FOR PREOPERATIVE SIMULATION

(75) Inventors: Yoshinobu Kubota, Yokohama (JP);
Kazuhide Makiyama, Yokohama (JP);
Manabu Nagasaka, Kamakura (JP);
Kentaro Takanami, Kamakura (JP);
Masato Ogata, Kamakura (JP)

(73) Assignee: Mitsubishi Precision Co., Ltd., Tokyo (JP)

( * ) Notice: Subject to any disclaimer, the term of this patent is extended or adjusted under 35 U.S.C. 154(b) by 464 days.

(21) Appl. No.: 12/998,797

(22) PCT Filed: Nov. 30, 2009

(86) PCT No.: PCT/JP2009/070441
§ 371 (c)(1),
(2), (4) Date: Jun. 1, 2011

(87) PCT Pub. No.: WO2010/064718
PCT Pub. Date: Jun. 10, 2010

(65) Prior Publication Data
US 2011/0238395 A1    Sep. 29, 2011

(30) Foreign Application Priority Data
Dec. 2, 2008   (JP) ................................. 2008-307116

(51) Int. Cl.
*G06T 17/00* (2006.01)
*G06G 7/58* (2006.01)
*G06K 9/00* (2006.01)

(52) U.S. Cl.
USPC ............................. 345/424; 703/11; 382/131

(58) Field of Classification Search
None
See application file for complete search history.

(56) References Cited

U.S. PATENT DOCUMENTS

2008/0247622 A1* 10/2008 Aylward et al. ............... 382/131
2009/0018808 A1*  1/2009 Bronstein et al. ............... 703/11

FOREIGN PATENT DOCUMENTS

JP   2008-134373    6/2008
WO   WO 2006/013813   2/2006

OTHER PUBLICATIONS

International Search Report dated Jan. 12, 2010 issued in corresponding PCT Application No. PCT/JP2009/070441.

(Continued)

*Primary Examiner* — Carlos Perromat
*Assistant Examiner* — Nurun N Flora
(74) *Attorney, Agent, or Firm* — Kenyon & Kenyon LLP

(57) ABSTRACT

The invention is directed to the provision of a method for generating a model for a preoperative simulation, wherein the method includes: a first step of constructing volume data for necessary organs by acquiring geometrical information from a medical image; a second step of manipulating the volume data to reposition and reorient an operator-designated organ to achieve a position and orientation appropriate for a surgical operation; a third step of generating a blood-vessel model, depicting a blood vessel to be joined to the designated organ, so as to match the position and orientation of the designated organ; a fourth step of generating volume data by forming a fat model of prescribed thickness around a prescribed organ contained in the earlier constructed volume data, after the blood-vessel model has been joined to the designated organ; a fifth step of thereafter meshing the organ represented by the generated volume data; a sixth step of manipulating a template model of a prescribed shape by using a template, and arranging the template model around the generated blood-vessel model; and a seventh step of generating a line-segment model based on the thus arranged template model.

6 Claims, 7 Drawing Sheets

(56) References Cited

OTHER PUBLICATIONS

Kazuhide Makiyama, "Mission rehearsal type simulator for laparoscopic surgery using patient specific image data", Japanese Journal of Endourology and ESWL, vol. 21, No. 4, Nov. 2008 (received date), p. 147.

* cited by examiner (a) CT DATA (b) VOLUME DATA (c) CHANGING OF KIDNEY POSITION

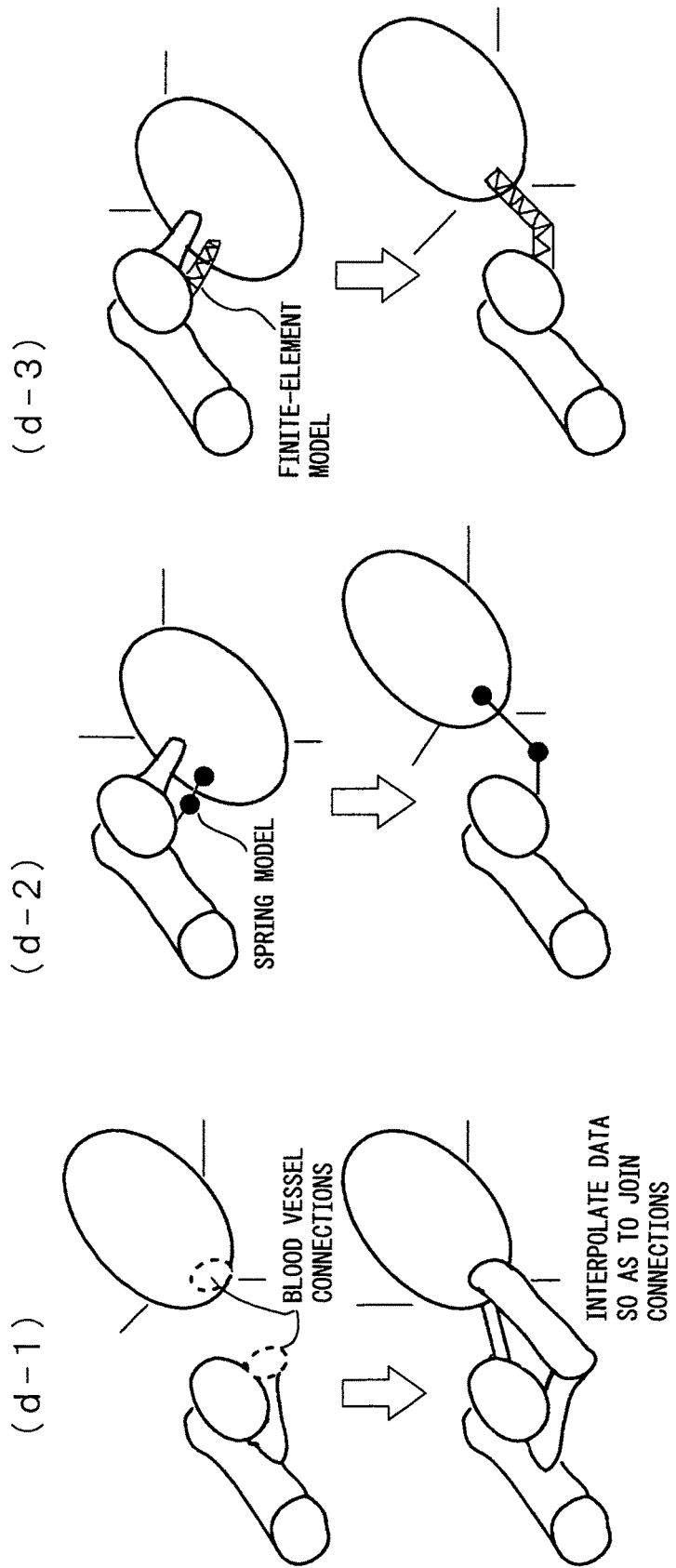

(e)

(f)

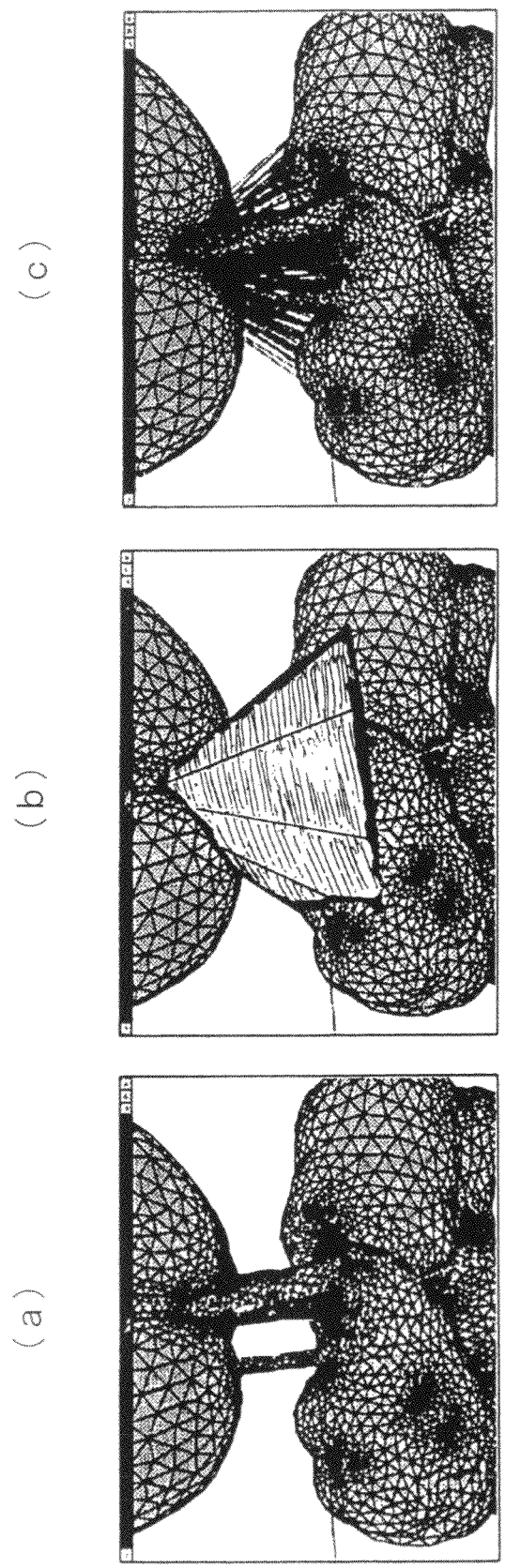

METHOD FOR GENERATING MODEL FOR PREOPERATIVE SIMULATION

This application is a national stage application of International Application No. PCT/JP2009/070441, filed 30 Nov. 2009, which claims priority to Japanese Application No. 2008-307116, filed 02 Dec. 2008, which is incorporated by reference in its entirety.

TECHNICAL FIELD

The present invention relates to a method for generating a model for a preoperative simulation by using a medical image such as a CT or MRI image taken of a patient who is about to undergo a surgical operation.

BACKGROUND ART

With advances in medical technology and medical instruments, many abdominal surgical operations have come to be performed using a laparoscope. Since laparoscopic surgery is performed by viewing a three-dimensional object displayed on a two-dimensional monitor screen, training is indispensable to the acquisition of the required skill. In actual laparoscopic surgery, the surgery must be planned so as to match each individual patient because the number of blood vessels, the directions of the blood vessels, and the positional relationship among organs, for example, the position and size of a tumor, differ from patient to patient.

One possible method to make a preoperative simulation possible is to use a simulator adapted based on information acquired of each individual patient.

To acquire information of each individual patient, it is common to use medical image data such as CT (Computed Tomography) or MRI (Magnetic Resonance Imaging) data, but in this case, only geometrical information can be acquired, and the physical and dynamical conditions cannot be acquired. Further, in laparoscopic surgery, the position or orientation of the patient during actual surgery is different from that of the patient during CT imaging, and thus the positional relationship changes. Furthermore, since the images of lymphatic vessels, membranes, etc., cannot be captured by CT, these parts cannot be modeled, resulting in the problem that a model that does not incorporate such parts is unsuitable for use in a preoperative simulation.

SUMMARY OF THE INVENTION

Problem to be Solved by the Invention

An object of the present invention is to provide a method for generating from a medical image a simulation model that matches the actual surgical conditions.

Means for Solving the Problem

A method for generating a model for a preoperative simulation, according to claim 1, includes: a first step of constructing volume data for necessary organs by acquiring geometrical information from a medical image; a second step of manipulating the volume data to reposition and reorient an operator-designated organ to achieve a position and orientation appropriate for a surgical operation; a third step of generating a blood-vessel model, depicting a blood vessel to be joined to the designated organ, so as to match the position and orientation of the designated organ repositioned and reoriented in the second step; a fourth step of generating volume data by forming a fat model of prescribed thickness around a prescribed organ contained in the volume data constructed in the first step, after the blood-vessel model generated in the third step has been joined to the designated organ; and a fifth step of meshing, after the fourth step, the organ represented by the generated volume data.

A method for generating a model for a preoperative simulation, according to claim 2, includes: a first step of constructing volume data for necessary organs by acquiring geometrical information from a medical image; a second step of manipulating the volume data to reposition and reorient an operator-designated organ to achieve a position and orientation appropriate for a surgical operation; a third step of generating a blood-vessel model, depicting a blood vessel to be joined to the designated organ, so as to match the position and orientation of the designated organ repositioned and reoriented in the second step; a fourth step of generating volume data by forming a fat model of prescribed thickness around a prescribed organ contained in the volume data constructed in the first step, after the blood-vessel model generated in the third step has been joined to the designated organ; a fifth step of meshing, after the fourth step, the organ represented by the generated volume data; a sixth step of manipulating a template model of a prescribed shape by using a template, and arranging the template model around the generated blood-vessel model; and a seventh step of generating a line-segment model based on the thus arranged template model.

A method for generating a model for a preoperative simulation, according to claim 3, includes: a first step of constructing volume data for necessary organs by acquiring geometrical information from a medical image; a second step of manipulating the volume data to reposition and reorient an operator-designated organ to achieve a position and orientation appropriate for a surgical operation; a third step of generating a blood-vessel model, depicting a blood vessel to be joined to the designated organ, so as to match the position and orientation of the designated organ repositioned and reoriented in the second step; a fourth step of generating volume data by forming a fat model of prescribed thickness around a prescribed organ contained in the volume data constructed in the first step, after the blood-vessel model generated in the third step has been joined to the designated organ; a fifth step of meshing, after the fourth step, the organ represented by the generated volume data; a sixth step of manipulating a template model of a prescribed shape by using a template, and arranging the template model around the generated prescribed organ model; and a seventh step of generating, based on the thus arranged template model, a membrane model that has a longitudinally extending line-segment model and laterally-connected information of the line-segment model.

A method for generating a model for a preoperative simulation, according to claim 4, is a method as claimed in any one of claims 1 to 3, wherein the blood-vessel model is generated by one of the following methods: the method in which a portion where the blood vessel was originally connected is geometrically extended and connected; the method in which the blood vessel is converted into a spring model, and simulation is performed; and the method in which the blood vessel is modeled by a finite-element model, and deformation simulation is performed using a finite-element method.

Advantageous Effect of the Invention

According to the method of claim 1 for generating a model for a preoperative simulation, since the designated organ is generated in a position and orientation appropriate for a surgical operation, and since the blood-vessel model to be joined to the designated organ is generated in a deformed shape with the designated organ held in that position and orientation, conditions close to those in actual surgery can be reproduced by simulation; furthermore, since the fat model is generated around the organ, an organ model closer to the actual organ can be reproduced.

According to the method of claim 2 for generating a model for a preoperative simulation, the following effect is offered in addition to that achieved in claim 1; i.e., since the lymphatic vessel which cannot be captured in a medical image such as a CT or MRI image can be generated based on the template model, conditions closer to those in actual surgery can be reproduced by simulation, and the efficiency of surgical training can thus be further enhanced.

According to the method of claim 3 for generating a model for a preoperative simulation, the following effect is offered in addition to that achieved in claim 1; i.e., since the membrane which cannot be captured in a medical image such as a CT or MRI image can be generated based on the template model, conditions closer to those in actual surgery can be reproduced by simulation, and the efficiency of surgical training can thus be further enhanced.

According to the method of claim 4 for generating a model for a preoperative simulation, the blood-vessel model can be generated in any one of claims 1 to 3 by one of the following methods. That is, according to the method in which the portion where the blood vessel was originally connected is geometrically extended and connected, the blood-vessel model can be generated in a simple manner. According to the method in which the blood vessel is converted into a spring model, the diameter of the blood vessel can be reduced according to the extended length at the time of the simulation. When the blood-vessel model is generated by modeling the blood vessel using a finite-element model, deformation simulation can be performed using the finite-element method at the time of the simulation.

BRIEF DESCRIPTION OF THE DRAWINGS

FIG. 3B is a diagram explaining the process of simulation model generation.

FIG. 4 is a diagram explaining the process of simulation model generation.

DESCRIPTION OF THE EMBODIMENTS

Embodiment 1

From the viewpoint of constructing the technical basis common to all surgical operations, the simplest possible surgical technique is considered here. More particularly, of various endoscopic surgeries, a surgery to remove all of a kidney (kidney removal) is considered. Two approaches are available for the kidney removal surgery: the peritoneal approach and the retroperitoneal approach. By considering the number of anatomical elements (kidney, ureter, renal artery and renal vein, aorta and vena cava and their associated blood-vascular system, and organs adjacent to the kidney) of a patient that become necessary for simulation, the retroperitoneal approach which can reduce the number of organs to be modeled is employed here.

The procedure of the retroperitoneal approach is divided into the following three steps.

1. Reach the region to be operated on, through small incisions made in body surface, and lift kidney to provide space for surgery.

2. Expose blood vessel and clip and cut it.

3. Remove kidney.

The most important point in the surgery here is to perform the treatment without damaging the blood vessel in the step 2. In view of this, a technique that involves exposing the blood vessel is considered in this embodiment. Therefore, the following describes how the kidney is held in the lifted position and how a model is generated for the lymphatic vessels that are not captured in a medical image such as a CT image.

Figure 1A:
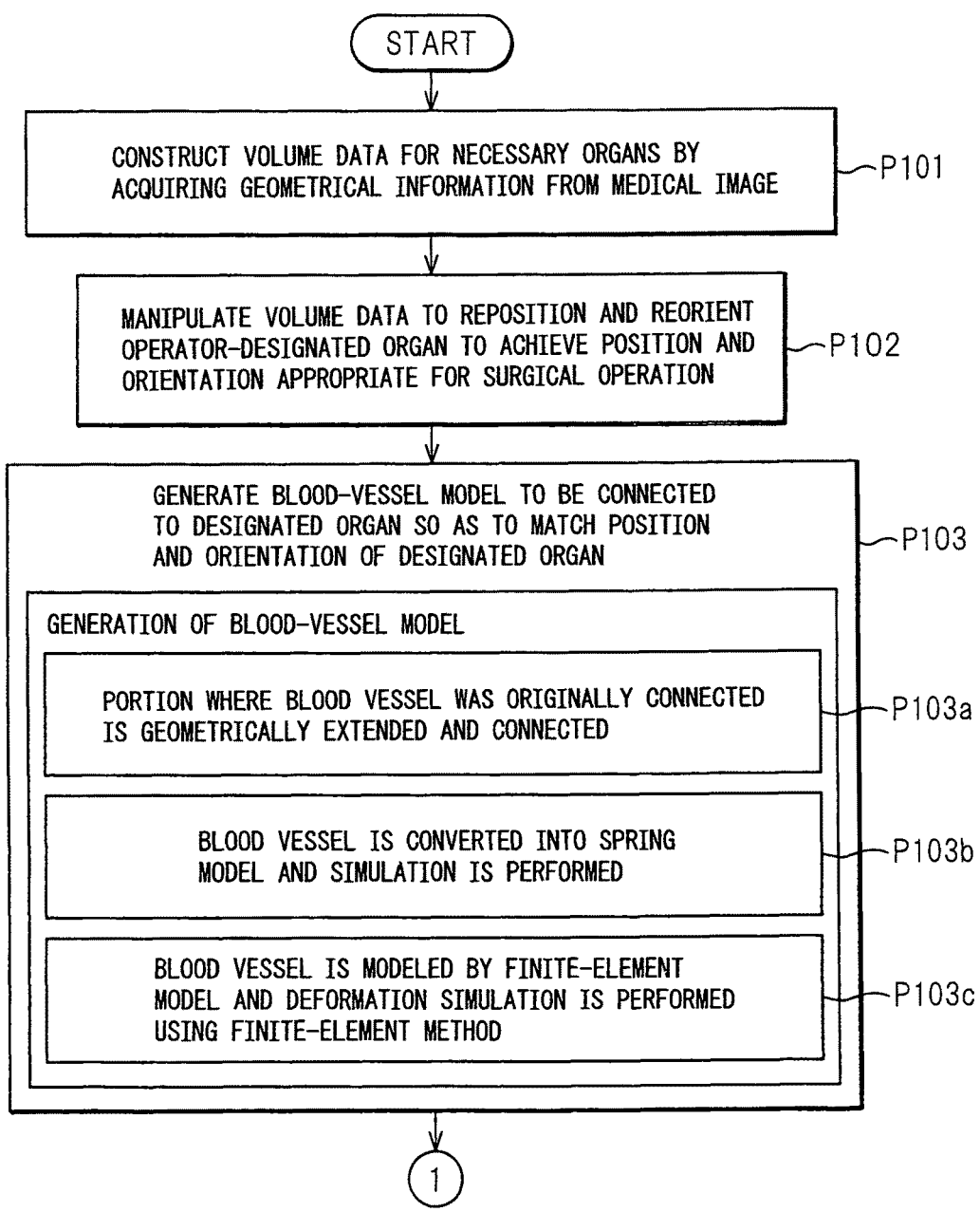
FIG. 1A is a flow diagram explaining the method for generating a model for a preoperative simulation.
Figure 1B:
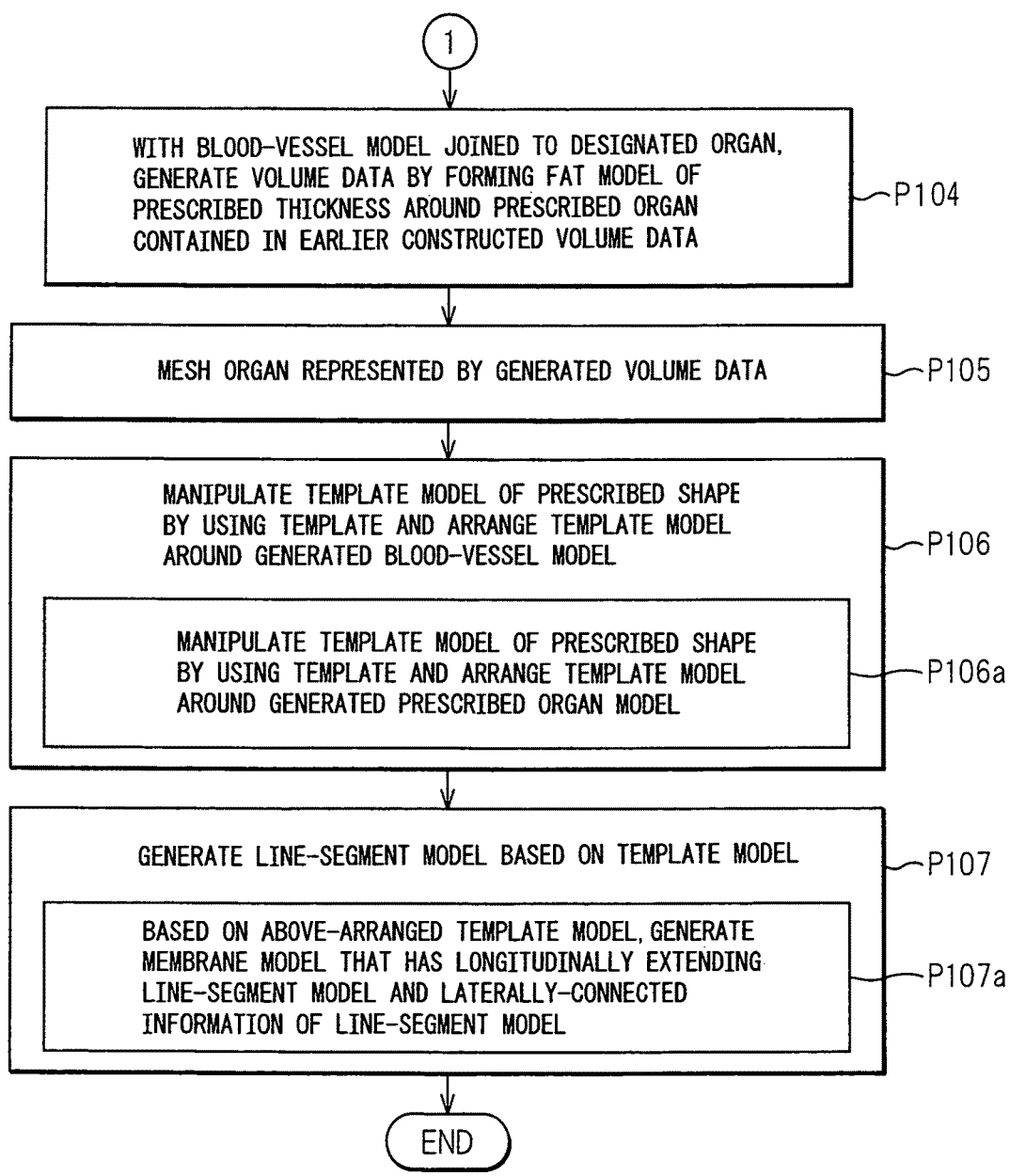
FIG. 1B is a flow diagram explaining the method for generating a model for a preoperative simulation.
Figure 2:
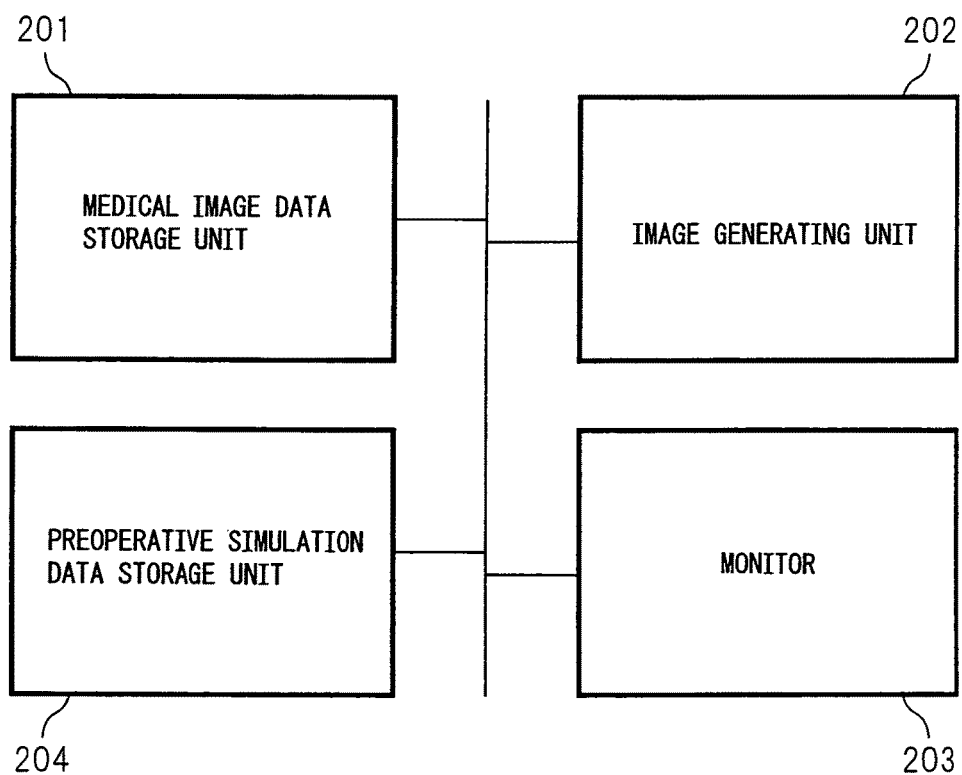
FIG. 2 is a functional block diagram of the apparatus for carrying out the present invention.
Figure 3A:
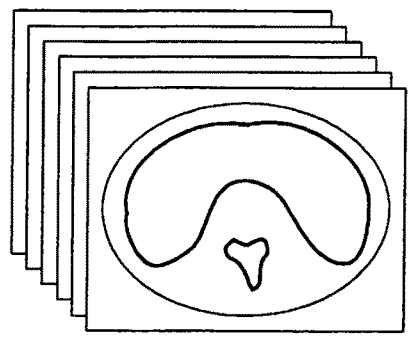
FIG. 3A is a diagram explaining the process of simulation model generation.
Figure 3A:
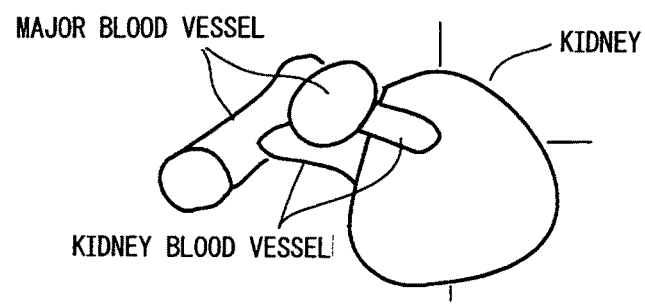
Figure 3A:
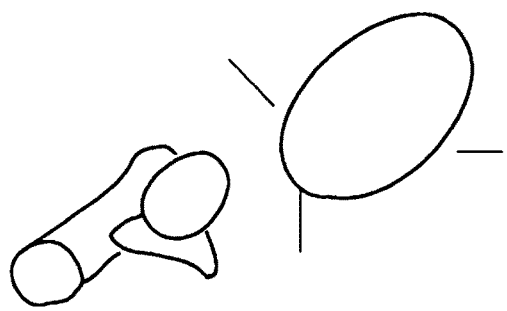
Figure 3C:
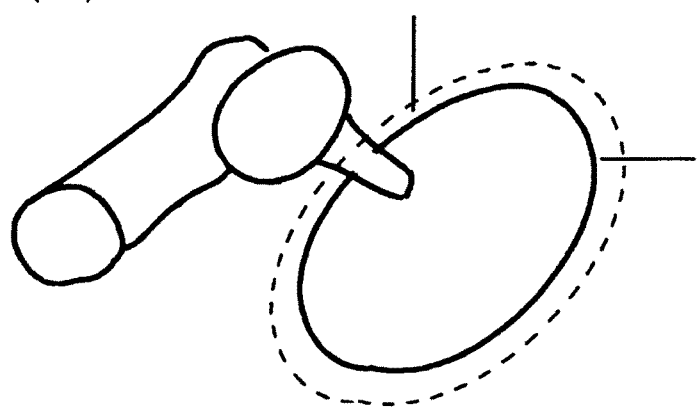
FIG. 3C is a diagram explaining the process of simulation model generation.
Figure 3C:
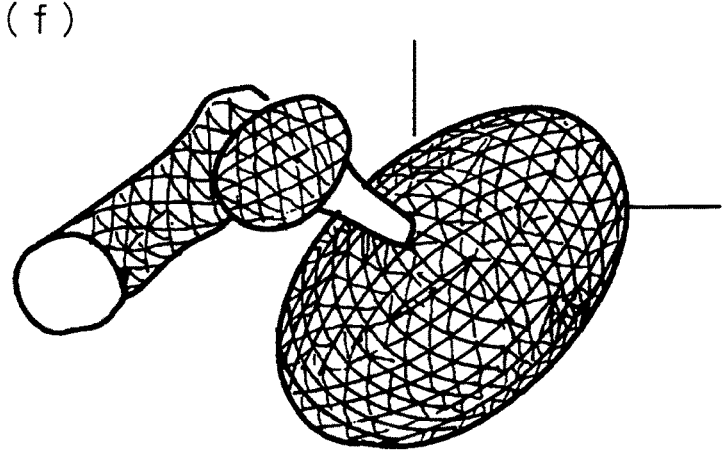

FIGS. 1A and 1B are flow diagrams for explaining the method of the present invention. FIG. 2 is a functional block diagram of an apparatus for carrying out the present invention, and FIGS. 3A, 3B, and 3C and FIG. 4 are diagrams for explaining the process of simulation model generation.

In FIG. 2, reference numeral 201 is a medical image data storage unit, 202 is an image generating unit, 203 is a monitor, and 204 is a preoperative simulation data storage unit.

(Generation of Kidney Lift Model)

The medical image data storage unit 201 stores the original data for medical images captured, for example, of a patient to be operated on. The medical image data storage unit 201 captures images of body parts, including organs, by scanning in thin slices the cross section of the patient to be operated on, extracts each body part (organ) in two dimensions based on geometrical information, arranges the organs in accordance with their predetermined positions relative to each other, and stacks the images of the thin slices one on top of another to construct three-dimensional volume data (P101 in FIG. 1) (part (a) of FIG. 3A). The three-dimensional volume data is stored in the medical image data storage unit 201 in a storage area different from the storage area where the original data for the medical images is stored.

The operator retrieves from the medical image data storage unit 201 the medical image data of the patient to be operated on. The image generating unit 202 extracts the organs (kidney, ureter, renal artery and renal vein, aorta and vena cava and their associated blood-vascular system, and organs adjacent to the kidney) situated in the predetermined area containing the kidney, the intended organ for which the data has been retrieved, and displays them on the monitor 203 in accordance with their predetermined positions relative to each other (part (b) of FIG. 3A). The operator moves and rotates the intended organ, i.e., the kidney, by selecting it from among the organs displayed on the monitor 203 (P102 in FIG. 1) (part (c) of FIG. 3A).

The volume data has an ID assigned to each organ; here, the original volume data can be written as ID=F(x,y,z), and the processed volume data as ID=G(x,r,z). When this move/rotate transformation is expressed in the form of a matrix $R_{ID}$, the relationship between F and G is given as $R_{ID}F=G$, so that G can be obtained as $G=R_{ID}^{-1}F$.

The move is performed to move the kidney from behind it toward the operator in order to provide a space for surgery during actual surgery; basically, the position to which the kidney is to be moved is calculated based on a predetermined set value (given by an empirical value set by a physician), but in this embodiment, provisions are made to be able to adjust the position through a GUI in order to accommodate differences between individuals, such as the age and weight. This moved position data is stored in the preoperative simulation data storage unit 204

Next, the kidney blood vessel is generated to correspond with the movement of the kidney (P103 in FIG. 1A). The state that can be obtained from the CT image is the state in which the load is already applied among the respective organs, but the dynamical conditions of the load cannot be obtained from the CT image. Accordingly, blood-vessel deformation simulation is difficult to achieve, unless some assumption is introduced. In the present embodiment, the blood vessel is generated using a computer program by assuming the state in which the blood vessel is stretched in a straight line as it is pulled by the kidney. The portion where the kidney blood vessel is joined to the kidney is detected from the volume data, and the portion where the kidney blood vessel is joined to the major blood vessel is detected from the monitor screen; then, columns connecting them are newly formed and modeled, and the thus modeled kidney blood vessel is joined to the kidney and the major blood vessel. In this case, the kidney blood vessel is formed by two columns connected by a portion where it contacts the vena cava (part (d-1) of FIG. 3B). This kidney blood-vessel model data is stored in the preoperative simulation data storage unit 204.

The generation of the kidney blood vessel can be accomplished by i) a method in which the portion where the blood vessel was originally connected is geometrically extended and connected (P103*a* in FIG. 1A), or by one of the following two methods.

ii) The blood vessel is converted into a spring model, and simulation is performed (P103*b* in FIG. 1A).

The blood vessel is simulated by several line segments, and elongation simulation is performed using the spring model (part (d-2) of FIG. 3B). The diameter of the blood vessel is reduced in inversely proportional relationship with the extended length in accordance with the law of conservation of volume. The calculation result of this simulation is stored in the preoperative simulation data storage unit 204.

iii) The blood vessel is converted into a finite-element model, and simulation is performed (P103*c* in FIG. 1A).

The blood vessel is modeled by a finite-element model, and deformation simulation is performed using the finite-element method (part (d-3) of FIG. 3B). The calculation result of this simulation is stored in the preoperative simulation data storage unit 204.

Next, for the volume data, the geometrical information is taken as input information, and the thickness is determined based on the anatomical properties, thereby forming a fat model around the designated organ (P104 in FIG. 1B). Anatomically, fat is classified into fat that is formed around an organ or blood vessel and fat that is formed so as to extend over more than one organ. By designating the organ around which the fat is to be formed and specifying its thickness, the shape of the designated organ is expanded by the thickness, and fat data is thus added (part (e) of FIG. 3C). The finite-element model is generated using a computer program by meshing the thus generated volume data on a tetrahedron (P105 in FIG. 1B) (part (f) of FIG. 3C). This fat model data is stored in the preoperative simulation data storage unit 204.

(Generation of Lymphatic Vessel Model)

In the surgery of the present embodiment, the main point is to expose the blood vessel. Before the treatment, the blood vessel is hidden behind such tissues as lymphatic vessels and fat; accordingly, a training simulation is provided that aims to expose the blood vessel by removing these tissues little by little without damaging the blood vessel. However, for the lymphatic vessels whose images cannot be captured by CT or the like, there is no data based on which to generate a model. In view of this, a line-segment model is generated that reflects the general characteristics that the lymphatic vessels run in a clustered fashion along the blood vessel and that the lymphatic vessels are fibrous.

A template model of a prescribed shape is manipulated using a template, and is arranged around the blood-vessel model of the volume data generated in the above-described P105 (a portion thereof is shown in enlarged form in part (a) of FIG. 4) (P106 in FIG. 1B) (part (b) of FIG. 4). The template has the shape of, for example, an elliptical column or an elliptical cone. The operator arranges this template around the blood vessel model on which the lymphatic vessel model is to be formed. The position, orientation, and shape of the elliptical column or elliptical cone can be set through a GUI.

Based on the elliptical column or elliptical cone arranged around the blood-vessel model, the line-segment model is generated (P107 in FIG. 1B). Using a computer program, the line-segment model is arranged so as to cover the surface of the elliptical column or elliptical cone from the inside thereof and so as to run along the direction of the blood vessel (part (c) of FIG. 4). Since the lymphatic vessels are fibrous, the line-segment model generated here is a directed line-segment model. This line-segment model data is stored in the preoperative simulation data storage unit 204.

(Generation of Membrane Model)

When provided with laterally-connected information, the line-segment model becomes a membrane model. A template model of a prescribed shape is manipulated using a template, and is arranged around the prescribed organ model generated in the above-described P105 (P106*a* in FIG. 1B) (part (b) of FIG. 4). The template has a shape suitable, for example, as the membrane of the organ. The operator arranges this template around the organ model on which the membrane is to be formed. The position, orientation, and shape of the template can be set through a GUI.

Based on the template arranged around the organ model, the line-segment model is generated that has laterally-connected information (P107*a* in FIG. 1B). Using a computer program, the line-segment model having the laterally-connected information is arranged so as to cover the surface of the membrane model. This membrane model data is stored in the preoperative simulation data storage unit 204.

Using a simulation program, the operator can perform the preoperative simulation by retrieving the thus created simulation model from the preoperative simulation data storage unit 204.

DESCRIPTION OF REFERENCE NUMERALS

201 . . . MEDICAL IMAGE DATA STORAGE UNIT
202 . . . IMAGE GENERATING UNIT
203 . . . MONITOR
204 . . . PREOPERATIVE SIMULATION DATA STORAGE UNIT

What is claimed is:

1. A method for generating a model for a preoperative simulation, comprising:
a first step of constructing volume data for necessary organs by acquiring geometrical information from a medical image;
a second step of manipulating said volume data to reposition and reorient an operator-designated organ to achieve a position and orientation appropriate for a surgical operation;
a third step of generating a blood-vessel model, depicting a blood vessel to be joined to said designated organ, so as to match the position and orientation of said designated organ repositioned and reoriented in said second step;

a fourth step of generating volume data by forming a fat model of prescribed thickness around a prescribed organ contained in said volume data constructed in said first step, after said blood-vessel model generated in said third step has been joined to said designated organ; and a fifth step of meshing, after said fourth step, the organ represented by said generated volume data.

2. A method for generating a model for a preoperative simulation, comprising:

a first step of constructing volume data for necessary organs by acquiring geometrical information from a medical image;

a second step of manipulating said volume data to reposition and reorient an operator-designated organ to achieve a position and orientation appropriate for a surgical operation;

a third step of generating a blood-vessel model, depicting a blood vessel to be joined to said designated organ, so as to match the position and orientation of said designated organ repositioned and reoriented in said second step;

a fourth step of generating volume data by forming a fat model of prescribed thickness around a prescribed organ contained in said volume data constructed in said first step, after said blood-vessel model generated in said third step has been joined to said designated organ;

a fifth step of meshing, after said fourth step, the organ represented by said generated volume data;

a sixth step of manipulating a template model of a prescribed shape by using a template, and arranging said template model around said generated blood-vessel model; and a seventh step of generating a line-segment model based on said arranged template model.

3. A method for generating a model for a preoperative simulation, comprising:

a first step of constructing volume data for necessary organs by acquiring geometrical information from a medical image;

a second step of manipulating said volume data to reposition and reorient an operator-designated organ to achieve a position and orientation appropriate for a surgical operation;

a third step of generating a blood-vessel model, depicting a blood vessel to be joined to said designated organ, so as to match the position and orientation of said designated organ repositioned and reoriented in said second step;

a fourth step of generating volume data by forming a fat model of prescribed thickness around a prescribed organ contained in said volume data constructed in said first step, after said blood-vessel model generated in said third step has been joined to said designated organ;

a fifth step of meshing, after said fourth step, the organ represented by said generated volume data;

a sixth step of manipulating a template model of a prescribed shape by using a template, and arranging said template model around said generated prescribed organ model; and a seventh step of generating, based on said arranged template model, a membrane model that has a longitudinally extending line-segment model and laterally-connected information of said line-segment model.

4. A method for generating a model for a preoperative simulation as claimed in claim 1, wherein said blood-vessel model is generated by one of the following methods:

the method in which a portion where said blood vessel was originally connected is geometrically extended and connected;

the method in which said blood vessel is converted into a spring model, and simulation is performed; and the method in which said blood vessel is modeled by a finite-element model, and deformation simulation is performed using a finite-element method.

5. A method for generating a model for a preoperative simulation as claimed in claim 2, wherein said blood-vessel model is generated by one of the following methods:

the method in which a portion where said blood vessel was originally connected is geometrically extended and connected;

the method in which said blood vessel is converted into a spring model, and simulation is performed; and the method in which said blood vessel is modeled by a finite-element model, and deformation simulation is performed using a finite-element method.

6. A method for generating a model for a preoperative simulation as claimed in claim 3, wherein said blood-vessel model is generated by one of the following methods:

the method in which a portion where said blood vessel was originally connected is geometrically extended and connected;

the method in which said blood vessel is converted into a spring model, and simulation is performed; and the method in which said blood vessel is modeled by a finite-element model, and deformation simulation is performed using a finite-element method.

* * * * *

UNITED STATES PATENT AND TRADEMARK OFFICE
CERTIFICATE OF CORRECTION

| | |
|---|---|
| PATENT NO. | : 8,681,152 B2 |
| APPLICATION NO. | : 12/998797 |
| DATED | : March 25, 2014 |
| INVENTOR(S) | : Yoshinobu Kubota et al. |

It is certified that error appears in the above-identified patent and that said Letters Patent is hereby corrected as shown below:

In the Specification

Column 5, line 3, change "unit 204" to -- unit 204. --

Signed and Sealed this
Second Day of September, 2014

Michelle K. Lee
*Deputy Director of the United States Patent and Trademark Office*